US009554952B2

(12) United States Patent
Rönnberg et al.

(10) Patent No.: US 9,554,952 B2
(45) Date of Patent: Jan. 31, 2017

(54) ABSORBENT ARTICLE

(75) Inventors: Peter Rönnberg, Mölndal (SE); Kenneth Strannemalm, Floda (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 317 days.

(21) Appl. No.: 14/130,577

(22) PCT Filed: Jun. 29, 2012

(86) PCT No.: PCT/SE2012/050742
§ 371 (c)(1),
(2), (4) Date: Jan. 2, 2014

(87) PCT Pub. No.: WO2013/006130
PCT Pub. Date: Jan. 10, 2013

(65) Prior Publication Data
US 2014/0155856 A1    Jun. 5, 2014

(30) Foreign Application Priority Data

Jul. 1, 2011    (CN) .......................... 2011 1 0189269

(51) Int. Cl.
*A61F 13/15*    (2006.01)
*A61F 13/62*    (2006.01)
(Continued)

(52) U.S. Cl.
CPC .......... *A61F 13/622* (2013.01); *A61F 13/4902* (2013.01); *A61F 13/49011* (2013.01);
(Continued)

(58) Field of Classification Search
CPC .............. A61F 13/496; A61F 13/49011; A61F 13/4902; A61F 13/49003; A61F 2013/49033
(Continued)

(56) References Cited

U.S. PATENT DOCUMENTS

| 4,964,860 A | 10/1990 | Gipson et al. |
| 4,964,960 A | 10/1990 | Keating et al. |

(Continued)

FOREIGN PATENT DOCUMENTS

| CN | 202191413 U | 4/2012 |
| EP | 1 142 547 A1 | 10/2001 |

(Continued)

OTHER PUBLICATIONS

International Search Report (PCT/ISA/210) mailed on Oct. 2, 2012, by the Swedish Patent Office as the International Searching Authority for International Application No. PCT/SE2012/050742.

(Continued)

*Primary Examiner* — Jacqueline Stephens
(74) *Attorney, Agent, or Firm* — Buchanan Ingersoll & Rooney PC

(57) ABSTRACT

An absorbent article includes a belt placed around the waist of the wearer and an absorbent pad attached to the belt, wherein the pad includes a chassis having a topsheet, a backsheet and an absorbent core, wherein the absorbent pad is attached to a surface of the belt attaching arrangements provided on each corner of the front portion and the rear portion of the pad, wherein the waist elastic is provided at the waist portion of at least one of the front and rear portion and is movable between a contracted condition in which the topsheet and/or backsheet exhibit(s) pleats and a fully stretched condition in which the pleats of the topsheet and/or backsheet are fully stretched out, wherein the elastic force from said waist elastic is within the range of from 2 N to 7 N when the elastic is in the fully stretched condition.

13 Claims, 7 Drawing Sheets

(51) Int. Cl.
  *A61F 13/505* (2006.01)
  *A61F 13/64* (2006.01)
  *A61F 13/56* (2006.01)
  *A61F 13/496* (2006.01)
  *A61F 13/49* (2006.01)

(52) U.S. Cl.
  CPC .. *A61F 13/49012* (2013.01); *A61F 13/49017* (2013.01); *A61F 13/505* (2013.01); *A61F 13/5644* (2013.01); *A61F 13/64* (2013.01); *A61F 13/49003* (2013.01); *A61F 13/496* (2013.01); *A61F 2013/49033* (2013.01)

(58) Field of Classification Search
  USPC .......... 604/385.24, 385.26, 385.27, 385.29, 604/385.3, 396, 401, 392
  See application file for complete search history.

(56) References Cited

U.S. PATENT DOCUMENTS

| | | |
|---|---|---|
| 5,151,092 A | 9/1992 | Buell et al. |
| H1440 H | 5/1995 | New et al. |
| 5,906,604 A | 5/1999 | Rönnberg et al. |
| 5,971,970 A | 10/1999 | Carlbark et al. |
| 6,334,858 B1 | 1/2002 | Rönnberg et al. |
| 6,845,283 B2 | 1/2005 | Popp et al. |
| 7,794,442 B2 | 9/2010 | Roehrl et al. |
| 7,850,673 B1 | 12/2010 | Carlbark et al. |
| 7,875,014 B2 | 1/2011 | Hendren et al. |
| 2002/0151858 A1 | 10/2002 | Karami et al. |
| 2004/0049168 A1 | 3/2004 | Gompel et al. |
| 2004/0082932 A1 | 4/2004 | Lauritzen |
| 2004/0186456 A1 | 9/2004 | Nawata et al. |
| 2005/0027279 A1 | 2/2005 | Minato et al. |
| 2006/0116656 A1 | 6/2006 | Hendren et al. |
| 2007/0293835 A1 | 12/2007 | Roehrl et al. |
| 2008/0026178 A1 | 1/2008 | Stupperich et al. |
| 2009/0157028 A1 | 6/2009 | Back |
| 2012/0035572 A1 | 2/2012 | Ichikawa et al. |
| 2014/0142534 A1* | 5/2014 | Carney ............ A61F 13/51462 604/391 |

FOREIGN PATENT DOCUMENTS

| | | |
|---|---|---|
| EP | 1 011 583 B1 | 10/2002 |
| EP | 1 906 897 A1 | 4/2008 |
| EP | 1 661 540 B1 | 7/2009 |
| EP | 2 415 440 A1 | 2/2012 |
| JP | H03-136652 A | 6/1991 |
| JP | H11-19129 A | 1/1999 |
| JP | 2001-513670 A | 9/2001 |
| JP | 2005-046225 A | 2/2005 |
| JP | 2007-511326 A | 5/2007 |
| JP | 2007-175302 A | 7/2007 |
| JP | 2008-521458 A | 6/2008 |
| JP | 2008-538984 A | 11/2008 |
| RU | 2 269 991 C2 | 2/2006 |
| RU | 2 316 300 C2 | 2/2008 |
| WO | WO 91/08725 A1 | 6/1991 |
| WO | WO 94/26224 A1 | 11/1994 |
| WO | WO 94/26225 A1 | 11/1994 |
| WO | 98-37847 A1 | 9/1998 |
| WO | WO 99/21522 A1 | 5/1999 |
| WO | WO 99/60972 A1 | 12/1999 |
| WO | 0143672 A2 | 6/2001 |
| WO | WO 2004/069122 A1 | 8/2004 |
| WO | 2005-051264 A1 | 6/2005 |
| WO | 2006-056396 A1 | 6/2006 |
| WO | WO 2006/118709 A1 | 11/2006 |

OTHER PUBLICATIONS

Written Opinion (PCT/ISA/237) mailed on Oct. 2, 2012, by the Swedish Patent Office as the International Searching Authority for International Application No. PCT/SE2012/050742.

Written Opinion of the International Preliminary Examining Authority (PCT/IPEA/408) mailed on Jul. 5, 2013, by the European Patent Office as the International Preliminary Examining Authority for International Application No. PCT/SE2012/050742.

International Preliminary Report on Patentability (PCT/IPEA/409) completed on Oct. 2, 2013, by the European Patent Office as the International Preliminary Examining Authority for International Application No. PCT/SE2012/050742.

Office Action issued on Mar. 25, 2015, by the Russian Federal Service for Intellectual Property in corresponding Russian Application No. 2014103244. (3 pages).

Office Action (Notice of Reasons for Rejection) issued on Sep. 7, 2015, by the Japanese Patent Office in corresponding Japanese Patent Application No. 2014-518500, and an English Translation of the Office Action. (10 pages).

Office Action (Notice of Reasons for Rejection) issued on Feb. 2, 2015, by the Japan Patent Office in corresponding Japanese Patent Application No. 2014-518500 (English Translation only). (4 pages).

* cited by examiner

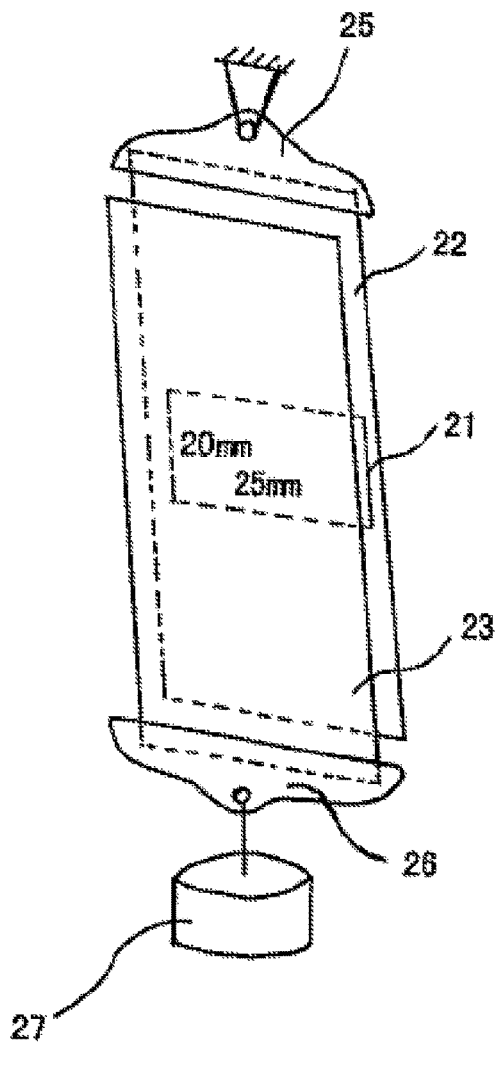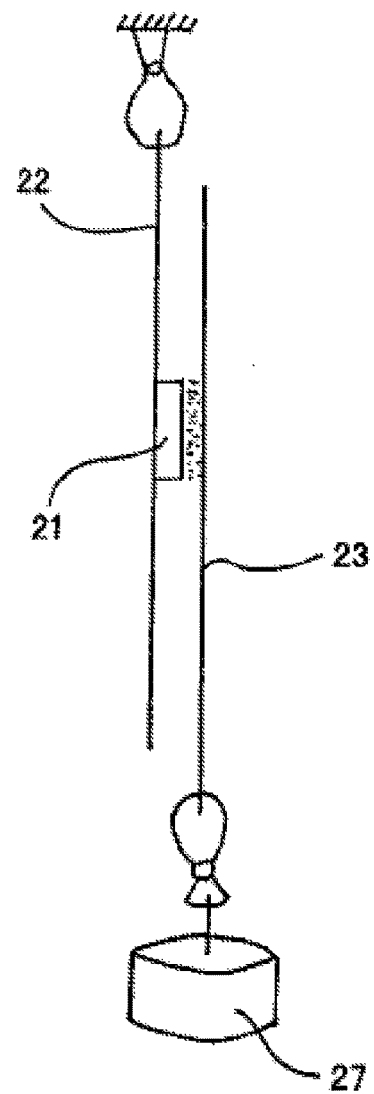
Figure 7a                    Figure 7b

_US 9,554,952 B2_

ABSORBENT ARTICLE

TECHNICAL FIELD

The present invention relates to an absorbent article with an absorbent pad and a separate belt, in particular to an absorbent article with waist elastics provided in the waist portions of the pad.

TECHNICAL BACKGROUND

It is known that absorbent articles, in the forms of diapers, pant diapers, or incontinent-protecting products, are generally used for babies and incontinent adults for the absorption of bodily exudates, such as blood, urine, sweat and faeces. Some of these absorbent articles are provided with a belt to be placed around the waist of the wearer to facilitate putting on and putting off of the articles.

There are two kinds of belts. One type of belt is integral with the pad and will be discarded together with the disposal article, see for example EP 1142547 A1. The belt may be an intact belt permanently attached to the pad. The belt may alternatively be in the form of two halves laterally extending from either side of the waist portions of the pad.

The other type of belt relates to a separate belt detachably attached to the pad, see for example WO99/21522, WO94/26224, WO94/26222, WO94/26225 and U.S. Pat. No. 4,964,960. The ends of the belt are provided with attaching elements, which are attached to each other when the belt is placed around the waist of the wearer. To put on the article on the wearer, one of the ends of the pad is detachably attached to the belt (this step will be omitted if the belt is integral with the pad). Then the pad is passed through between the legs of the wearer. Finally, the other free end of the pad is detachably attached to the belt. The attachment between the two ends of the belt as well as the attachment between the belt and the pad are generally obtained by hook & loop connections, which are known to the persons skilled in the art. Optionally, other fastening means such as adhesive bonding may also be used. The provision of a reusable separate belt is favorable in order to save material.

However, in the above mentioned articles, the waist portion of the pad is flat without any elastic. When attaching the pad to the belt, the pad is prone to be positioned correctly in transverse direction with offset, such as in U.S. Pat. No. 4,964,860, since the attachment areas are small.

In view of this, some belts are provided with attaching indicators to show where the pad should be attached. Some pads are provided with extendable waist portions in order to adjust the attaching positions between the pad and the belt.

In U.S. Pat. No. 5,971,970 a garment system with an absorbent pad and a separate belt is disclosed. The longitudinal ends of the pad are provided with hook element strips to be attached to loop elements on the belt or to the belt itself. In addition, in view of the comfort, the belt is provided with a non-attachment zone, the length of which is defined to not be larger than the distance between the two hook elements on the waist portion of the pad in order to obtain comfort and precise positioning. Especially, FIG. 7 of U.S. Pat. No. 5,971,970 exhibits an absorbent garment comprising hook attachment areas and waist elastics 15 between the hook attachment areas in each end of the article.

As to the purpose of providing the waist elastics, U.S. Pat. No. 5,971,970 just mentions that "fitment of the chassis correctly then requires merely extending the strip 6' away from each other until they have a separating y greater than the length x of the zone 7".

U.S. Pat. No. 5,971,970 does not mention the strength of the hook & loop connection between the pad and the belt. Rather, U.S. Pat. No. 5,971,970 only mentions that the belt contains a nonwoven material to strengthen the attachment, but the relations between the shear force from the waist elastic and the peel force required to separate the hook element and the loop element are not discussed. When the peel force is too low, the pad may undesirably detach from the belt, which results in leakage and contamination. Too high peel force, on the other hand, will make it difficult to detach the pad from the belt when needed and may thus result in undesired damage of the belt in the case where it is a reusable belt.

SUMMARY

In view of the above mentioned problems with existing absorbent articles, the disclosure provides an absorbent article with well controlled hook-loop connection strength between the pad and the belt.

More specifically, the disclosure provides an absorbent article comprising an absorbent pad and a separate belt, where hook elements are arranged in the corners of the pad and these are to be attached to loop elements on the belt. At least one of the longitudinal ends of the pad comprises a waist elastic between the hook elements. Said waist elastic is stretched when the first end of the pad is attached to the belt and the reaction force, i.e. the shear force from the waist elastic, is then applied on the hook & loop connections. The reaction force contributes to strengthen the peel strength of the hook-loop connections so that they not easily separate accidentally.

Too low reaction force cannot increase the peel strength of the hook & loop connection and too high reaction force will break the attachment between the hook & loop connection by its own shear force.

Therefore, an object of the disclosure is to provide an absorbent article with the shear force from the waist elastic within a desirable range.

To achieve this object, the disclosure relates to an absorbent article comprising an absorbent pad and a separate belt, which is intended to be placed around the waist of the wearer and to which the absorbent pad is detachably attached, wherein the pad comprises a chassis having a liquid-permeable topsheet, a liquid-impermeable backsheet and an absorbent core between the topsheet and the backsheet, and the absorbent pad is divided into a front portion, a rear portion and a crotch portion provided between the front portion and rear portion along its longitudinal direction, and is intended to be detachably attached at each longitudinal end to a surface of the belt oriented away from wearer using attaching arrangements (fastening means) provided at each corner of the front portion and the rear portion of the pad, characterized in that at least one of the front and rear portion is provided with a waist elastic arranged symmetrically on each side of the longitudinal center line and extending between the attaching arrangements in the transverse direction of the pad, wherein the waist elastic is provided at the waist portion of the at least one of the front and rear portion and is movable between a contracted condition in which the topsheet and/or backsheet exhibit(s) pleats and a fully stretched condition in which the pleats of the topsheet and/or backsheet are fully stretched out, wherein the elastic force from said waist elastic is within the range from 2 N to 7 N when the elastic is in the fully stretched condition.

In a particular embodiment, the elastic force form the waist elastic is within the range from 2.7 N to 7 N, more particularly within the range from 3.6 N to 7 N, when the elastic is in the fully stretched condition.

In particular, the attaching arrangement on the pad is in the form of hook & loop fastening means formed by hook elements (hook material) on the corners of the pad and loop elements (loop material) on the belt. Alternatively, loop elements may be provided on the corners of the pad and hook elements on the belt.

In the case that the corners of the pad are provided with hook elements, the belt may be a laminated belt formed by at least two layers, the outermost layer of which constitutes a nonwoven layer while the innermost layer forms a supporting layer to support the outer layer. In particular, the outer layer of the belt may be a carded nonwoven layer. In addition, the outer layer of the belt may be laminated to a spun bond support layer.

In particular, the hook element constitutes moulded hooks.

In one embodiment, the waist elastic is integrated with the absorbent pad.

In an alternative embodiment, the waist elastic is an element separately produced and attached to the pad with said attaching arrangement provided at its edges.

In order to improve reliability and convenience, the absorbent article of the invention provides a hook & loop connection that is strong enough to ensure that the hook elements and the loop elements not will be separated when the article is put on the wearer.

BRIEF DESCRIPTION OF THE DRAWINGS

The invention will now be explained in more detail with reference to certain non-limiting embodiments and with reference to the accompanying drawings, in which

FIG. 6b is a sectional view taken along the line A-A in FIG. 6a.

FIG. 7a shows the step of applying a shear force vertically on the hook & loop connection sample.

FIG. 7b is a side view of the hook & loop connection sample shown in FIG. 7a.

DETAILED DESCRIPTION OF THE PREFERRED EMBODIMENTS

Figure 1:
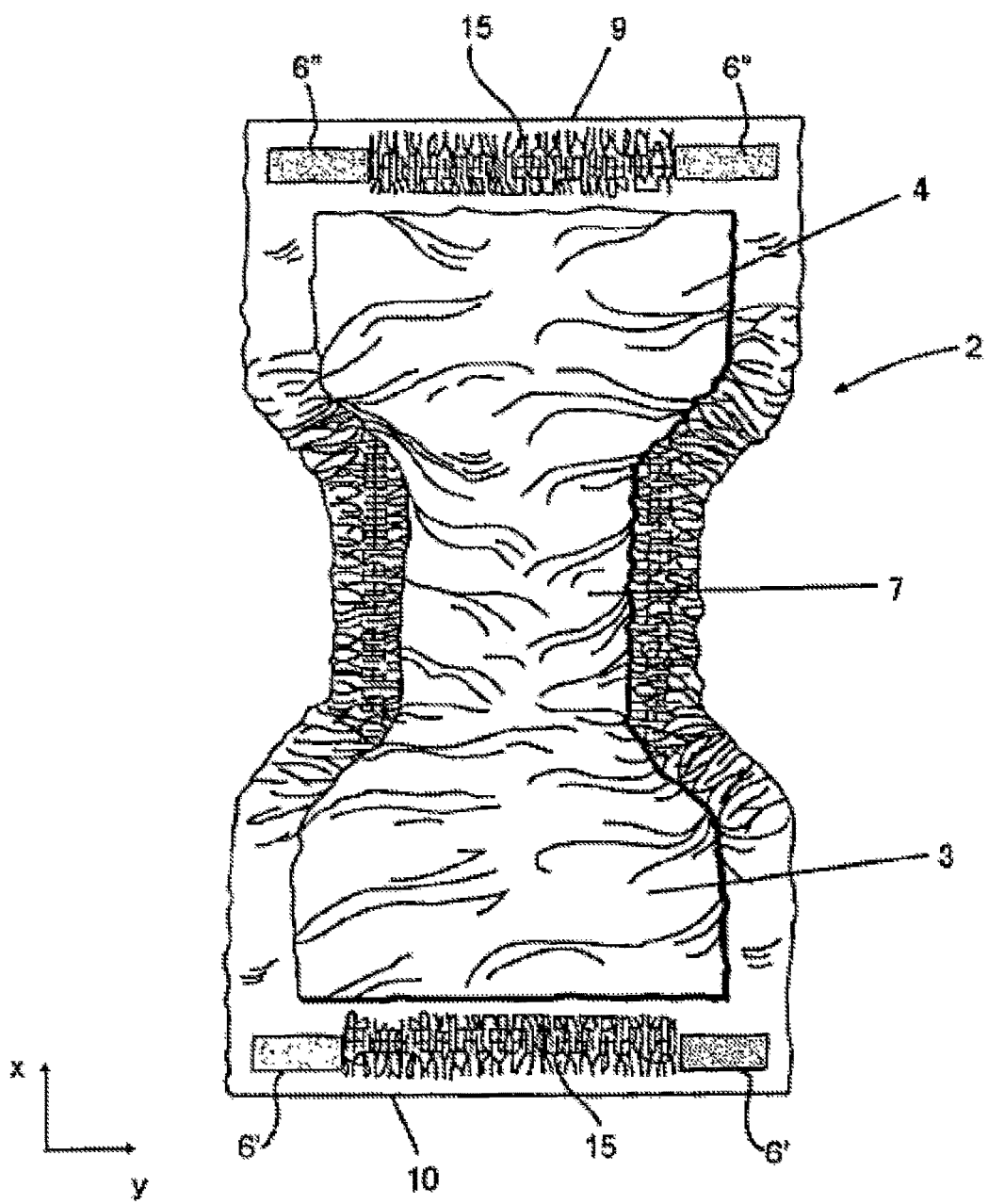
FIG. 1 shows an absorbent pad of an absorbent article according to an embodiment of the invention.
Figure 2:
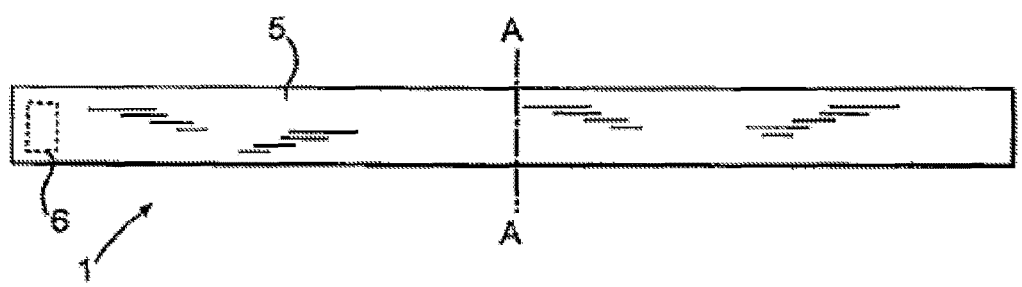
FIG. 2 shows a separate belt of to be used with the absorbent article shown in FIG. 1.

Embodiments of the present invention will be described below with reference to the drawings. The absorbent article of an embodiment of the present invention comprises an absorbent pad 2 as shown in FIG. 1 and a separate belt 1, as shown in FIG. 2, which is detachably attached to the pad. The belt 1 will be placed around the waist of the wearer when the article is to be used. The ends of the belt 1 are connected by attaching elements 6, such as hook element and loop element of the conventional hook & loop connection type to facilitate connection and disconnection of the pad 2 to the belt 1.

The absorbent pad 2 is extended along its longitudinal direction X and transverse direction Y. In particular, the absorbent pad is symmetrical along the longitudinal central line and the transverse central line in order for the absorbent pad to be attached to the belt at any of its longitudinal ends.

The absorbent pad 2 comprises a front portion 3, a rear portion 4 and a crotch portion 7 provided there between along the longitudinal direction X. The longitudinal ends 10, 9 of the front portion 3 and rear portion 4 may be detachably attached to the belt 1. Each of the corners of the longitudinal ends of the front portion 3 and the rear portion 4 is therefore provided with an attaching element 6', 6'' to be attached to the belt 1.

The absorbent pad 2, as shown in FIG. 1 comprises a liquid-permeable topsheet, a liquid-impermeable backsheet and an absorbent core located there between.

The topsheet of the absorbent pad 2 is the layer which lies in contact with the wearer's body when the pad is in use. As such, it should be soft, non-irritating and comfortable against the skin, and bodily fluid should be able to pass through it without hindrance. The topsheet may consist of a nonwoven material, e.g. spunbond, meltblown, carded, hydroentangled, wetlaid etc. Suitable nonwoven materials can be composed of natural fibers, such as wood pulp or cotton fibres, man-made fibres, such as polyester, polyethylene, polypropylene, viscose etc or from a mixture of natural and manmade fibres. The topsheet may further be composed of tow fibres, which may be bonded to each other in a bonding pattern. Further examples of materials suitable for top sheets are porous foams, apertured plastic films etc.

The backsheet of the absorbent pad is the layer which lies furthest away from the wearer's body when the pad is in use. To protect the wearer's garments from soiling, it should be liquid-impermeable, but desirably gas-permeable (i.e. breathable) to allow air and vapour to pass in and out of the pad so that the risk of warm, damp conditions which can arise in the pad is reduced. Typically, the backsheet is of a liquid-impervious material, such as a thin plastic film, e.g. a polyethylene or polypropylene film, a nonwoven material coated with a liquid-impervious material, a hydrophobic nonwoven material, which resists liquid-penetration or a laminate comprising plastic films and nonwoven materials. Examples of breathable backsheet materials are porous polymeric films, nonwoven laminates from spunbond and meltblown layers, laminates from porous polymeric films and nonwovens.

The absorbent core of the pad acts to receive and contain liquid and other bodily exudates and can be of any conventional kind. As such, it typically comprises absorbent material. Examples of commonly-occurring absorbent materials are cellulosic fluff pulp, tissue layers, highly-absorbent polymers (so called superabsorbents), absorbent foam materials, absorbent nonwoven materials or the like. It is common to combine cellulosic fluff pulp with superabsorbents in an absorbent body. It is also common to have absorbent cores comprising layers of different material with different properties with respect to liquid receiving capacity, liquid distribution capacity and storage capacity. The thin absorbent cores, which are common in for example baby diapers and incontinence guards, often comprise a compressed mixed or layered structure of cellulosic fluff pulp and superabsorbent.

The absorbent core may comprise one or more layers which are designed to improve the handling of bodily waste.

Such layers are designed to receive a large amount of liquid in a short period of time and distribute it. They may include so-called transfer, distribution, surge or acquisition layers, and are usually located between the topsheet and the absorbent core.

The topsheet and backsheet generally have similar extensions in the plane of the pad, while the absorbent core generally has an extension which is somewhat smaller. The top sheet and backsheet are joined to one another around the periphery of the absorbent core, so that the core is enclosed within the envelope formed by the topsheet and the backsheet. The absorbent core is at least located in the crotch portion 7 of the pad, and may also extend somewhat into the front portion 3 and rear portion 4. The topsheet and backsheet may be joined to one another by any means common in the art, e.g., ultrasonic welding, thermal welding or gluing.

The term "absorbent pad" is to be understood as meaning an article selected from the group consisting of diapers, male or female incontinence guards, pant diapers, etc. Such pads are used for the absorption of bodily exudates, such as blood, urine, sweat and faeces.

Especially, the attaching elements 6', 6" on the longitudinal ends 9, 10 of the front portion 3 and rear portion 4, respectively, may be hook elements of the conventional hook & loop connection type, while the belt 1 is provided with loop elements.

Alternatively, the belt 1 may be formed from a nonwoven material thereby forming said loop material. Thus, the belt itself is providing said loop elements, Alternatively, the belt may be a laminate formed by at least two layers. The wearer facing layer of the belt, also referred to as "supporting layer", should be soft, non-irritating and comfortable against the skin. The garment facing layer of the belt, i.e., outermost layer, is of non-woven materials. The outermost layer itself is used as a unitary loop element and is bonded to the supporting layer by any means known in the art such as ultrasonic welding, thermal welding, adhesive bonding etc.

The waist portion of the pad 2 comprises an extendable elastic element 15, also referred to "waist elastic", extending between the hook elements 6', 6' or 6", 6" in the center part of the waist area. The waist elastic 15 may be elastic wire, cord, strip, thread, etc, interposing the topsheet and the backsheet of the absorbent pad by sewing, gluing, thermal welding, etc, so that the topsheet and backsheet are pleated when the waist elastic is relaxed. Alternatively, the waist elastic may also be non-elastic nonwoven materials which is stretched or necked elasticized, or it may be an elastic laminate formed by laminating an elastic layer and a non-elastic layer.

Although the waist elastic 15 is shown in FIG. 1 as an integral part of the absorbent pad between the topsheet and the backsheet, it may also be an elongated waist elastic produced separately and then attached to the pad at the two longitudinal ends 9, 10 thereof by known means in the art, such as sewing, thermal welding, etc. with two attaching elements provided at the two ends of the separate waist elastic.

Specific embodiments of the present invention will be explained, by way of example, referring to a hook & loop connection between the belt and the pad provided by hook elements and loop elements. It should be understood that the hook & loop connection is just for illustration and not intended to limit the present invention. In fact, the hook elements may be displaced by adhesive strips while the corresponding loop elements may be displaced by landing surfaces which are attachable to the adhesive strips. It is also possible to switch the positioning of the hook element on the belt and the loop element on the pad.

The step of putting on the absorbent article will be described in detail referring to the hook & loop connection with hook elements on the pad and the belt itself used as loop elements.

First, the first end of the pad (for example, the longitudinal end 9) is attached to the belt.

In particular, the waist elastic is manually stretched out in transversal direction Y to a certain degree and then the hook elements are attached to the belt, i.e. the hook elements are pressed against the belt. However, the person attaching the pad to the wearer must be careful, not pressing too hard against the body of the wearer.

When the person performing the attachment of the first end of the pad to the belt releases his hands from the pad, the stretched out elastic contracts and thereby causes a reaction force on the hook elements, i.e. a shear force on each hook elements. This force strengthens the attachment (peel strength) of the hook & loop connection.

Then the second end or free end of the pad (for example the longitudinal end 10) is passed between the legs of the wearer. When performing this step there is no other force acting on the hook & loop connection of the attached first end than the shear force from the waist elastic.

If this shear force from the waist elastic is too low, the attachment strength of the hook & loop connection will be too low and there will be a risk for detachment, especially when peel forces are applied.

Peel forces are easily applied to the hook & loop connection when the free end of the pad is passed between the legs of the wearer. In addition, when the article is used, the weight caused by the absorption of exudates and the movement of the wearer will also tend to separate the hook elements from the loop elements.

On the other hand, if the waist elastics is too strong and have been stretched too much, the reaction forces on the hook & loop connections are too high and detachment will occur due to the reaction forces caused by the waist elastic itself.

Finally, the second end (free end) of the pad is attached to the belt.

The second end of the pad also comprises hook elements on each corner and waist elastic in between. Attachment of this end is done in the same way as when the first end was attached to the belt, i.e. the waist elastics is manually stretched out prior to attaching the hook elements to the loop material. In the same way as for the first end, the reaction force caused by the waist elastic acting on the hook & loop connections strengthen these hook & loop connection.

In particular, but not necessarily, the hook material may be of the type "Moulded Hook Faster" from Velcro (see http://www.fasteningsystems.com/ultra_mate_hth-_hook.html). These hooks have a "palm tree shape" (see http://www.velcro.com/index.php?page=business-products-all-ultra-mate). The hook density is 140±14 hooks/cm$^2$. Supplier is Velcro and the article code is "ULTRA-MATE HTH847®".

The belt material (loop material) may be a laminate comprising a loop layer and a support layer. The loop layer, the important layer from hook & loop connection point of view, constitutes in this case the outward oriented surface of the belt.

For example, the loop layer is a 30 g/m$^2$ carded nonwoven (2.2 dtex, 100% PP fibres), wherein the carded loop layer is bonded with a Tric Trac pattern.

Oriented toward the wearer is the support layer made of, for instance, spun bond, 100% PP fibres, with a surface weight of 50 g/m². The two layers constituting the laminate is in this case ultrasonic point bonded together, with approximate 4 mm between the points. Supplier of the laminate is Fiberweb Tenotex.

The test method to obtain the relationship between the shear force from the waist elastic and the peel force of the hook & loop connection will be described in detailed with reference to FIGS. 4-8.

Figure 4:
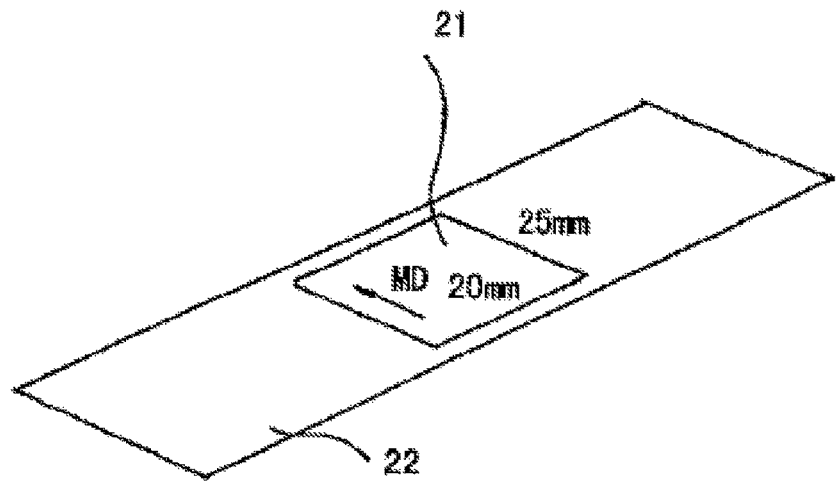
FIG. 4 shows the step of attaching a hook material on a carrier material.

In the first step, a piece of hook material 21 is attached to a carrier material 22, as shown in FIG. 4.

The carrier material 22 may be a PE film, a nonwoven, a tissue or the like which is strong enough. The hook material 21 is prepared by cutting a piece with the dimensions 25×20 mm from a roll of hook material wherein the dimension of 25 mm is in the machine direction MD. Then the hook material 21 is attached to the carrier material 22, by gluing, by using a double sided tape (Avery Dennison FT324) or the like, in a manner so that the hook material 21 is oriented on the carrier material 22 with its machine direction directed as shown in FIG. 4.

Figure 5:
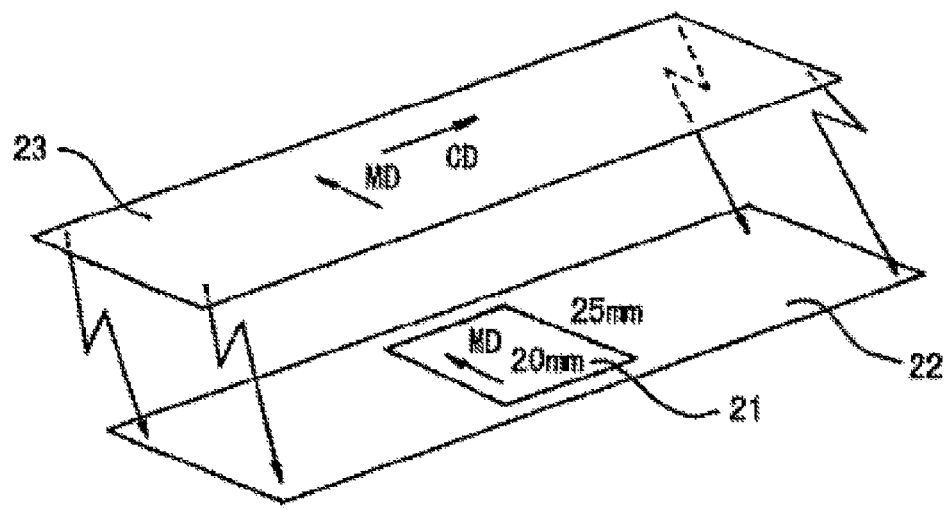
FIG. 5 shows the step of attaching a loop material on the hook material.

Then, a loop material 23 is prepared by cutting from a roll of loop material. The loop material 23 is placed over the hook material 21 in a manner so that the loop material 23 is oriented with its cross and machine direction (CD and MD) directed as shown in FIG. 5.

A hook & loop connection sample is thereby completed.

In the next step, pressure is applied on the hook & loop connection sample by a cylindrical weight 24 of 2 kg with 95 mm in diameter φ and 50 mm in length w, as shown in FIG. 6. The surface of the weight 24 is made of rubber with a hardness of A80 shore.

The cylindrical weight 24 is rolled once over the hook & loop connection in forward direction and then once rolled back over the sample again at a roll speed of 300 mm/min in order to obtain a firm hook & loop connection.

Figure 6A:
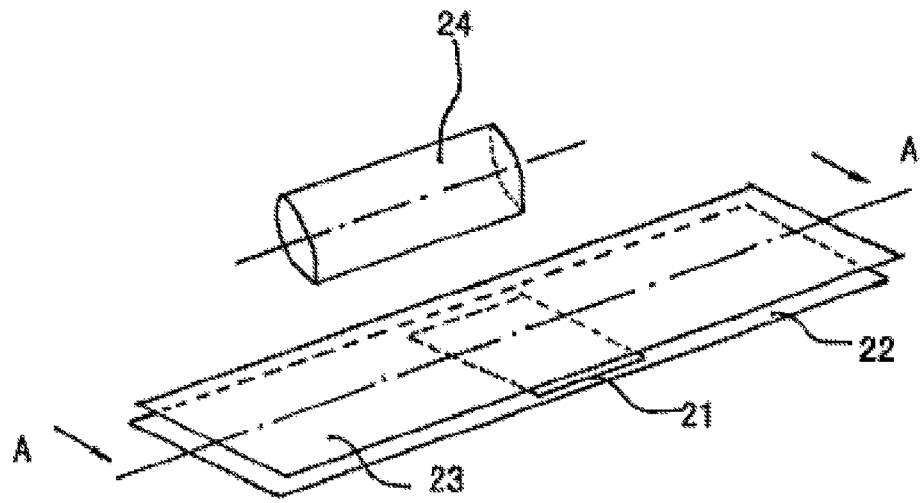
FIG. 6a shows the step of applying a pressure on the hook & loop connection sample.
Figure 6B:
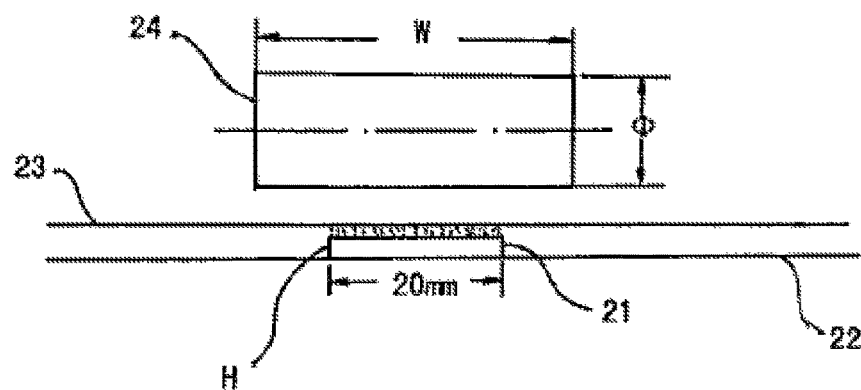
Figure 8:
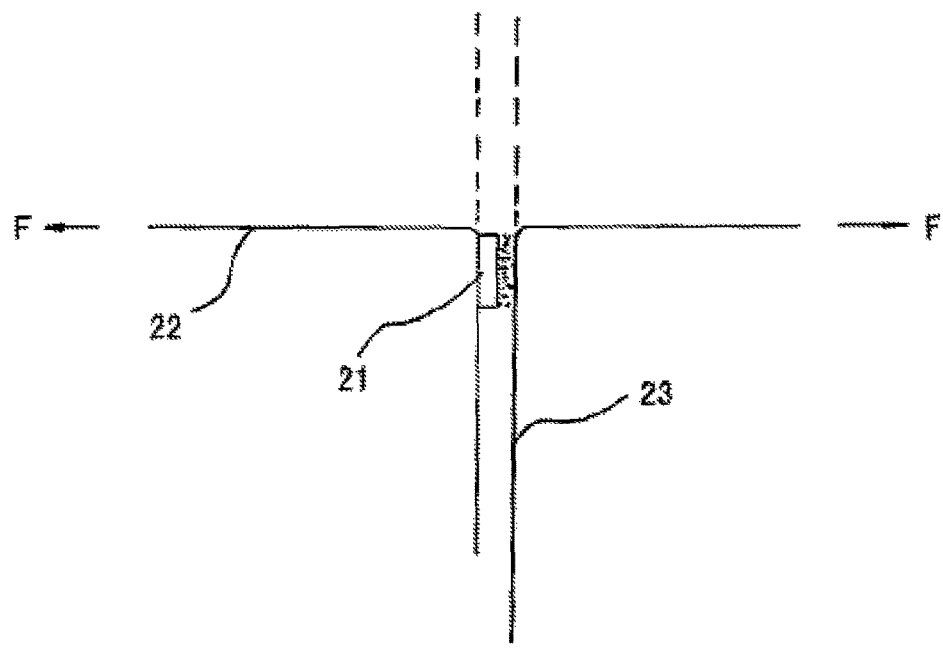
FIG. 8 shows the step of applying a peel force to the hook & loop connection sample.

FIG. 6b is a sectional view taken along a line A-A of FIG. 6a. As can be seen in FIG. 6b, the hook element 21 (20 mm wide) has a certain height H. This means that the full weight (2 kg) of the cylindrical weight is concentrated on the 20 mm wide hook element 21 when the cylindrical weight 24 rolls on the hook material 21.

With the above method, different samples representing different waist elastic forces can be prepared.

In the next step, a shear force is, as shown in FIGS. 7a and 7b, applied on the hook & loop connection sample prepared as described above.

The shear force is vertically applied to the hook & loop connection sample by two clamps. A first clamp 25 is connected to the carrier material 22 from above and a second clamp 26 is connected to the loop material 23 from below. A weight 27 is applied vertically to the second clamp 26 for 60 seconds. Different weights are applied to the different samples representing different waist elastic forces. The samples are here prepared in five groups. The weights vertically applied to each group of samples are here 0 g, 200 g, 300 g, 600 g and 1000 g, respectively.

Finally, a peel force is applied to the hook & loop connection sample while the sample is undergoing a certain shear force. Then the force F required to separate the hook element and the loop material (the peel strength of the sample) is measured and recorded. In the peel force test, an Instron, Lloyd tensile tester is used. The Crosshead speed is 300 mm/min.

The resulting peel forces of said five groups are listed in Tables 1-5, respectively.

TABLE 1

Peel forces at shear force from the waist elastic provided without any weight

| sample | Maximum load |
|---|---|
| 1 | 0.86 |
| 2 | 0.88 |
| 3 | 0.64 |
| 4 | 0.93 |
| 5 | 1.25 |
| 6 | 0.83 |
| 7 | 0.62 |
| 8 | 1.03 |
| 9 | 0.74 |
| 10 | 0.63 |
| Mean | 0.84 |
| Std Dev | 0.19873 |
| Minimum | 0.62 |
| Maximum | 1.25 |

TABLE 2

Peel forces at shear force from the waist elastic provided by a weight of 200 g

| sample | Maximum load |
|---|---|
| 1 | 1.12 |
| 2 | 1.50 |
| 3 | 1.05 |
| 4 | 0.71 |
| 5 | 1.22 |
| 6 | 0.68 |
| 7 | 1.42 |
| 8 | 0.82 |
| 9 | 0.62 |
| Mean | 1.02 |
| Std Dev | 0.32689 |
| Minimum | 0.62 |
| Maximum | 1.50 |

TABLE 3

Peel forces at shear force from the waist elastic provided by a weight of 300 g

| sample | Maximum load |
|---|---|
| 1 | 0.89 |
| 2 | 0.94 |
| 3 | 1.87 |
| 4 | 0.90 |
| 5 | 2.24 |
| 6 | 1.68 |
| 7 | 1.25 |
| 8 | 1.70 |
| 9 | 1.19 |
| 10 | 1.87 |
| 11 | 0.90 |
| Mean | 1.40 |
| Std Dev | 0.48419 |
| Minimum | 0.89 |
| Maximum | 2.24 |

TABLE 4

Peel forces at shear force from the waist elastic provided by a weight of 600 g

| sample | Maximum load |
|---|---|
| 1 | 2.28 |
| 2 | 2.32 |

TABLE 4-continued

Peel forces at shear force from the waist elastic provided by a weight of 600 g

| sample | Maximum load |
| --- | --- |
| 3 | 2.32 |
| 4 | 1.58 |
| 5 | 2.14 |
| 6 | 1.88 |
| 7 | 1.04 |
| 8 | 1.64 |
| 9 | 0.93 |
| Mean | 1.79 |
| Std Dev | 0.53522 |
| Minimum | 0.93 |
| Maximum | 2.32 |

TABLE 5

Peel forces at shear force from the waist elastic provided by a weight of 1000 g

| sample | Maximum load (N) |
| --- | --- |
| 1 | 2.05 |
| 2 | 3.02 |
| 3 | 1.91 |
| 4 | 2.13 |
| 5 | 2.83 |
| 6 | 3.06 |
| 7 | 3.02 |
| 8 | 2.69 |
| 9 | 2.28 |
| 10 | 1.94 |
| 11 | 2.75 |
| 12 | 1.91 |
| 13 | 2.90 |
| 14 | 3.05 |
| 15 | 2.55 |
| 16 | 1.63 |
| Mean | 2.48 |
| Std Dev | 0.49603 |
| Minimum | 1.63 |
| Maximum | 3.06 |

Figure 3:
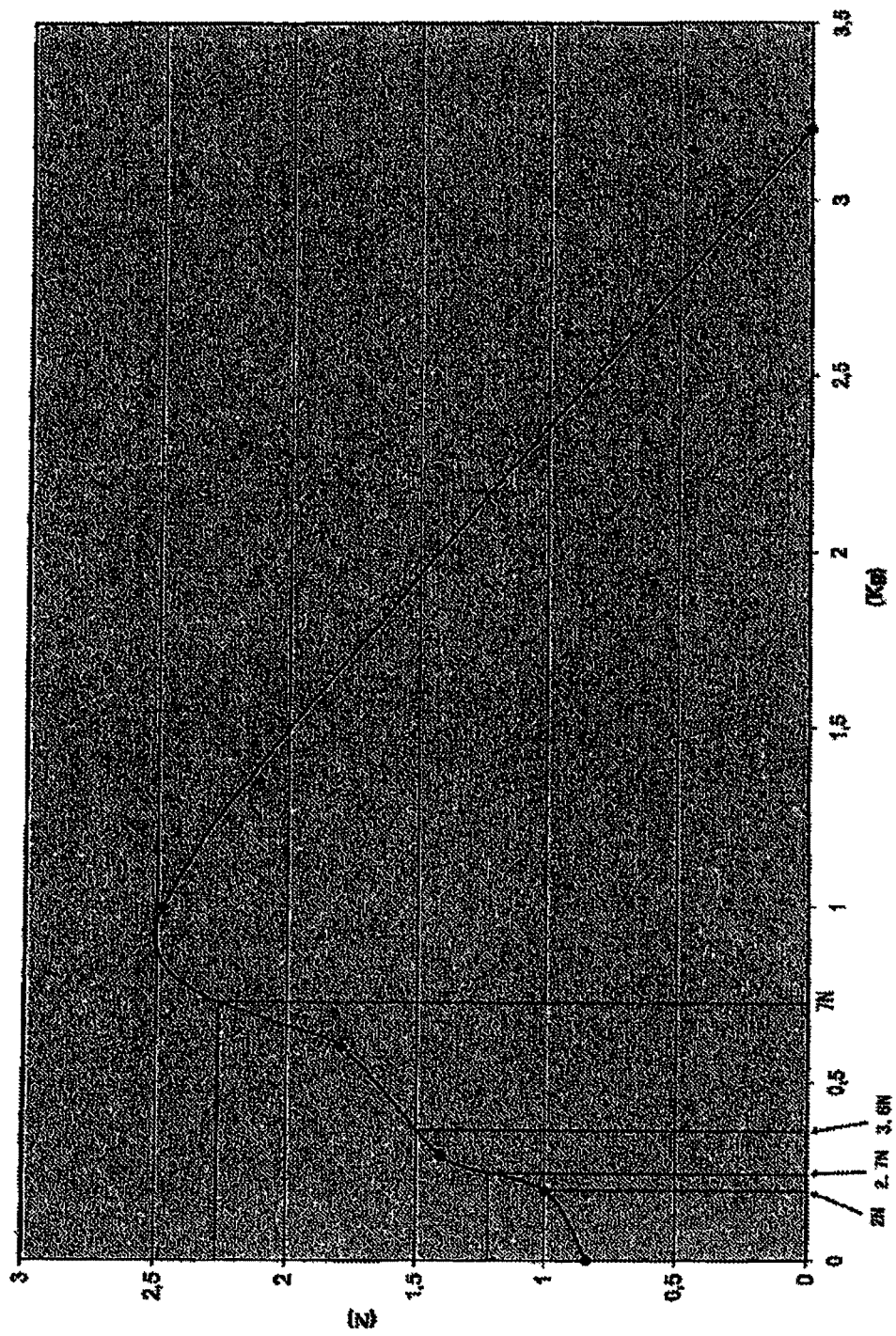
FIG. 3 shows the relation, based on several measurements, between the shear force from the waist elastic and the peel force required to separate the hook & loop connection.

Based on the data obtained above, the inventors summarize the relationship between the shear force from the waist elastic and the peel force of the hook & loop connection, which is shown in FIG. 3. It can be seen from FIG. 3 that too high shear force means that there is a risk that the hook & loop connection breaks due to the waist elastic force itself. According to the disclosure, the shear force is limited to be within the range of from 2 N to 7 N, in particular within the range of from 2.7 N to 7 N, such as within the range of from 3.6 N to 7 N, when the waist elastic is fully stretched out. The shear forces in these ranges will not cause the hook element to accidentally separate from the loop material or damage the belt when separating the pad from the belt.

According to an embodiment of the present invention, the controlling of the shear force is implemented during the manufacturing of the absorbent pad. When forming the waist elastic, the elastic wire, cord, thread or strip, or laminate elastics is stretched to achieve a tensile force of about 2 N to 7 N, and is then bonded to the flat topsheet and/or backsheet in the said stretched state at 2 N to 7 N in order to form the finished waist elastic 15. When the waist elastic 15 is relaxed, the topsheet and/or backsheet assume a pleated shape. When pulling the waist portion of the pad and stretching out the topsheet and/or backsheet again to make them flat, i.e. the waist elastic cannot be stretched further, the shear force from the waist elastic will be within the range of from 2 N to 7 N.

Whilst particular embodiments of the invention have been described above, it is to be understood that these are in no way limiting for the scope of the invention which is defined by the claims appended hereto.

The invention claimed is:

1. An absorbent article comprising an absorbent pad and a separate belt which is configured to be placed around the waist of the wearer and to which the absorbent pad is detachably attached, wherein the pad comprises a chassis having a liquid-permeable topsheet, a liquid-impermeable backsheet and an absorbent core between the top sheet and the backsheet, and wherein the absorbent pad is divided into a front portion, a rear portion and a crotch portion between the front portion and rear portion along the longitudinal direction, and wherein the absorbent pad is detachably attached at each of its longitudinal ends to a surface of the belt oriented away from the wearer using attaching arrangements provided at each corner of the front portion and the rear portion of the pad, the attaching arrangements are in the form of hook and loop connections;

wherein at least one of the front and rear portion is provided with a waist elastic arranged symmetrically on each side of the longitudinal center line and extending between the attaching arrangements in the transverse direction of the pad, wherein the waist elastic is provided at the waist portion of at least one of the front and rear portion and is movable between a contracted condition in which the topsheet or backsheet exhibits pleats and a fully stretched condition in which the pleats of the topsheet or backsheet are fully stretched out, wherein the elastic force from said waist elastic is within the range of from 2 N to 7 N when the elastic is in the fully stretched condition.

2. The absorbent article according to claim 1, wherein the elastic force from the waist elastic is within the range from 2.7 N to 7 N when the elastic is in the fully stretched condition.

3. The absorbent article according to claim 2, wherein the elastic force from the waist elastic is within the range from 3.6 N to 7 N when the elastic is in the fully stretched condition.

4. The absorbent article according to claim 1, wherein the attaching arrangement is in the form of a hook & loop connection and formed by hook elements provided on the corners of the pad and loop elements on the belt.

5. The absorbent article according to claim 4, wherein the belt is a laminated belt formed by at least two layers, the outermost layer of which constitutes a nonwoven layer providing said loop elements while the innermost layer forms a supporting layer to support the outer layer.

6. The absorbent article according to claim 5, wherein the outermost layer of the belt is a carded nonwoven layer.

7. The absorbent article according to claim 5, wherein the outermost layer of the belt is laminated to a spun bond support layer.

8. The absorbent article according to claim 4, wherein the hook elements constitute moulded hooks.

9. The absorbent article according to claim 1, wherein the attaching arrangements are formed by loop elements provided on the corners on the pad and hook elements on the belt.

10. The absorbent article according to claim 1, wherein the waist elastic is integrated with the absorbent pad.

11. The absorbent article according to claim 1, wherein the waist elastic is an element separately produced and attached to the pad with said attaching arrangement provided on its edges.

12. The absorbent article according to claim 1, wherein the waist elastic has a property of having been stretched to a tensile force of from 2 N to 7 N before having been attached to the front portion or the rear portion of the absorbent pad.

13. The absorbent article according to claim 1, wherein the waist elastic has a property of having been bonded to the front portion or the rear portion of the absorbent pad in a stretched state of the waist elastic at 2 N to 7 N.

* * * * *